United States Patent [19]

Speck

[11] Patent Number: 5,906,942
[45] Date of Patent: May 25, 1999

[54] METHOD FOR PREPARING STABLE COAGULATION CONTROLS

[75] Inventor: Roy E. Speck, Indianapolis, Ind.

[73] Assignee: Analytical Control Systems, Inc., Fishers, Ind.

[21] Appl. No.: 08/927,894

[22] Filed: Sep. 11, 1997

Related U.S. Application Data

[62] Division of application No. 08/458,632, Jun. 2, 1995, Pat. No. 5,721,140, which is a continuation of application No. 08/091,139, Jul. 14, 1993, abandoned, which is a continuation of application No. 08/004,188, Jan. 13, 1993, abandoned, which is a continuation of application No. 07/754,166, Sep. 3, 1991, abandoned, which is a continuation of application No. 07/383,004, Jul. 20, 1989, abandoned.

[51] Int. Cl.$^6$ .................................................. G01N 33/86
[52] U.S. Cl. .................................. 436/16; 436/8; 436/10; 436/18; 436/69; 435/13
[58] Field of Search .................... 436/8–18, 69; 525/408.1; 435/13

[56] References Cited

U.S. PATENT DOCUMENTS

| | | | |
|---|---|---|---|
| 3,947,378 | 3/1976 | Babson | 436/16 |
| 4,056,484 | 11/1977 | Heimburger et al. | 436/16 |
| 4,234,682 | 11/1980 | Bartl et al. | 435/13 |
| 4,271,122 | 6/1981 | Strassle et al. | 436/16 |
| 4,301,028 | 11/1981 | Bartl et al. | 436/8 |
| 4,382,028 | 5/1983 | Paget | 530/364 |
| 4,409,334 | 10/1983 | Lill et al. | 436/8 |
| 4,455,377 | 6/1984 | Finnerty et al. | 436/69 |
| 4,624,927 | 11/1986 | Fukushima et al. | 436/11 |
| 4,632,907 | 12/1986 | Sato et al. | 436/10 |
| 4,643,976 | 2/1987 | Hoskins | 436/15 |
| 4,720,787 | 1/1988 | Lipscomb | 600/369 |
| 4,731,330 | 3/1988 | Hill et al. | 436/16 |
| 4,877,741 | 10/1989 | Babcock et al. | 436/8 |
| 5,055,412 | 10/1991 | Proksch | 436/69 |
| 5,071,961 | 12/1991 | Kraus et al. | 530/384 |

OTHER PUBLICATIONS

Brozovic, et al., *Journal of Clinical Pathology*, 26:1973, pp. 857–863.
Radcliffe, et al., *Methods in Enzymology*, XLV (B), 1976, pp. 49–56.
Koide, et al., *Methods in Enzymology*, XLV (B), 1976, pp. 65–73.
Fujikawa, et al., *Methods in Enzymology*, XLV (B), 1976, pp. 74–83.
Legaz, et al., *Methods in Enzymology*, XLV (B), 1976, pp. 83–89.
Fujikawa, et al., *Methods in Enzymology*, XLV (B), 1976, pp. 89–95.
Jesty, et al., *Methods in Enzymology*, XLV (B), 1976, pp. 95–107.
Colman, et al., *Methods in Enzymology*, XLV (B), 1976, pp. 107–122.
Mann, *Methods in Enzymology*, XLV (B), 1976, pp. 123–156.
Miller, *Methods in Enzymology*, XIX, 1970, pp. 140–145.
Magnusson, *Methods in Enzymology*, XIX, 1970, pp. 157–184.
Fujikawa, et al., *Biochemsitry*, 11:26, 1972, pp. 4882–4891.
Dupe, et al., *Biochemical Journal*, 133:1973, pp. 311–321.
Contant, et al., Thrombosis research, 31:1983, pp. 365–374.
Hemotec, Inc., 7103 S. Revere Pky, Englewood, CO 80112, product bulletin describing CLOTtrac™ HR Control.
Kendall McGaw Laboratories, Inc., Irvine, CA 92714, product bulletin describing Monitoring Anticoagulation Using the ACTester™/AACTest™ System.
International Technidyne Corporation, 23 Nevsky Street, Edison, NJ 08820, product bulletin describing Hemochron® Coagulation Controls and Tests.
Gajewski, et al., *American Journal of Veterinary Research*, 32:3, 1971, pp. 405–409.
Greene, et al., *American Journal of Veterinary Research*, 42:12, 1981, pp. 2170–2177.

*Primary Examiner*—Harold Y. Pyon
*Attorney, Agent, or Firm*—Kenyon & Kenyon

[57] ABSTRACT

A method for preparing a coagulation control sample which is stable in the absence of buffer and which has a clotting time within the range of normal human clotting times for reproducibly monitoring coagulation capability in a human patient comprising (a) collecting blood from a mammalian animal, (b) removing red blood cells from the blood to produce mammalian plasma, and (c) adding to the plasma an amount of at least one non-primate mammalian plasma that has been adsorbed with a coagulation factors II, VII, IX and X adsorbent prior to addition of the plasma to the mammalian plasma.

6 Claims, No Drawings

METHOD FOR PREPARING STABLE COAGULATION CONTROLS

This application is a division of Ser. No. 08/458,632 filed Jun. 2,1995, now U.S. Pat. No. 5,721,140; which is a continuation of Ser. No. 08/091,139 filed Jul. 14, 1993, now abandoned; which is a continuation of Ser. No. 08/004,188 filed Jan. 13, 1993, now abandoned; which is a continuation of Ser. No. 07/754,166 filed Sep. 3, 1991, now abandoned; which is a continuation of Ser. No. 07/383,004 filed Jul. 20, 1989, now abandoned.

BACKGROUND OF THE INVENTION

The present invention relates generally to blood coagulation, and more particularly to improved blood coagulation controls which demonstrate superior stability, and also sensitivity to variation in reagents used in coagulation tests.

The need for stable and reliable blood coagulation controls is well documented. The continued and increased use of oral anticoagulants for treatment and management of various thrombo-embolytic conditions today, more than ever, is a driving force for their development. As is known, overdosage of anticoagulants, commonly the coumarin derivatives, can lead to serious complications, including hemorrhage from peptic ulcers, as well as other gastrointestinal complications. On the other hand, maintenance of too low a level of anticoagulant reduces or eliminates the efficacy of the prescribed treatment.

It is therefore extremely important that anticoagulant levels be reliably monitored, and, as such, a voluminous body of art has developed documenting attempts of those in the field to produce stable and reliable controls, as well as reagents, to aid in monitoring anticoagulant activity.

For example, U.S. Pat. No. 3,947,378 to Babson discloses a process for producing a control plasma deficient in Factors II, VII, IX, and X which involves treating to plasma with 20 to 22% by weight of barium sulfate at ambient temperature and then removing the adsorbent from the adsorbed plasma. The Babson patent reports that abnormal control plasmas produced by mixing the so-adsorbed plasma with normal plasma are more stable after reconstitution and give more uniform results in the activated partial thromboplastin time (APTT) procedure after storage of up to eight hours or more.

S. Zucker, M. H. Cathey, and B. West, *Preparation of Quality Control Specimens for Coagulation*, Amer. J. Clin Path., June 1970, Vol. 53 pp. 924–927, reports a method for preparing lyophilized plasma sp for use as quality controls in coagulation testing. Zucker et al. report buffering the plasma specimens with N-2-hydroxyethylpiperazine-N'-2-ethanesulfonic acid (HEPES), which was reported to provide pH and enzyme stability for prothrombin times for eight hours at 25° C. An article by M. Brozovic, D. J. Howarth, L. P. van Halem Visser, and E. A. Loeliger, *Stability of Freeze-Dried Plasma Prepared from Patients on Oral Anticoagulants*, Journal of Clinical Pathology, 1973, Vol. 26, p. 857–963, reported as to the suitability of freeze-dried plasmas from patients on oral anticoagulants to serve as reference material in the calibration of thromboplastins used in the control of oral anticoagulant treatment. The authors studied plasmas from several plasma pools, developed by collecting from each patient 4.5 ml of blood into 0.5 ml of a solution formed by combining 44.62 g of HEPES buffer, 38.00 g trisodium citrate ($2H_2O$), and 0.5 ml aprotinin TRASYLOL (1000 u/ml), and then adding distilled water to 1000 ml. Individual samples were centrifuged, as were the subsequently pooled samples, whereafter 1 ml of 10% sodium azide was added per liter of plasma. Samples of the prepared plasmas were then either frozen or freeze-dried. The authors reported that the freeze-dried plasmas from patients on oral anticoagulants could be used to calibrate thromboplastins provided that they are used immediately after complete reconstitution or kept at 4° C. for use within four to six hours of reconstitution. The authors also reported that their plasma samples generally demonstrated varying levels and types of instability after reconstitution and storage at 4° C., 22° C., and 37° C. It was generally reported that this instability resulted after about twenty-four hours at the lower two temperatures and after about four to six hours at the higher 37° C. temperature.

U.S. Pat. No. 4,007,008 to Becker et al. describes a method for reducing enzyme activities in animal sum or plasma including the steps of raising the pH thereof to a level about that of normal serum by adding a base, and thereafter terminating the reaction or reduction of enzyme activities neutralizing the serum or plasma with an acidic medium.

Other general background can be found in U.S. Pat. No. 3,799,885 to Dennis et al. which discloses a calcium chloride test reagent buffered with HEPES buffer which is especially adapted for use in monitoring heparin therapy; in U.S. Pat. No. 4,301,028 to Bartl et al. which reports a control reagent for heparin activity determination; in U.S. Pat. No. 4,116,336 to Sorenson et al. which relates to a package containing a synthetic reference liquid for quality control and/or calibration of blood gas measuring equipment; and in P. S. Roberts, H. N. Hughes, and P. B. Fleming, *The Effects of Hepes Buffer on Clotting Tests, Assay of Factors V and VIII and on the Hydrolysis of Esters by Thrombin and Thrombokinase, Tbrombos, Haemostas*, (Stuttg.), 1976, Vol. 35, p. 202, wherein the authors report faster clotting in the presence of 50 mM HFPES buffer.

Another aspect of the prior art control plasmas is that a majority of them, especially those commercially available, consist of or otherwise comprise primate plasma, most commonly human. These plasmas present disadvantages in that they contain unstable human factors, particularly Factors V and VIII, and also present a greater risk to the preparer or user of the controls, since they may harbor active AIDS or hepatitis viruses.

In the face of the voluminous literature and other work relating to plasmas for coagulation controls, there still remains a need for a coagulation control which exhibits superior stability with respect to one-stage prothrombin times (PT), activated partial thromboplastin times (APTT), and Factor V and VIII activity values, as well as superior sensitivity to variations in clotting test reagents employed. Certain forms of improved controls would also significantly eliminate risk of AIDS or hepatitis contraction to those who prepare and use it. The applicant's invention, in its various aspects, addresses these matters.

SUMMARY OF THE INVENTION

Accordingly, one preferred embodiment of the applicant's invention relates to a stable coagulation control plasma comprising blood plasma, and effective amounts of (a) a buffer to maintain a physiological pH, (b) a protease inhibitor, and (c) a suitable stabilizing carbohydrate. In a preferred aspect the control has a total plasma component constituted substantially of non-primate plasma.

Another preferred embodiment of the applicant's invention relates to a coagulation control plasma having high stabilized levels of Factor V and VIII. This control comprises plasma and at least about 2 weight percent of a suitable carbohydrate. The plasma of this embodiment is derived from blood which has been collected directly from an animal source into a solution containing a buffer to maintain a physiological pH, a protease inhibitor, and citrate. The carbohydrate in the control is added after removal of red blood cells from the blood.

Another preferred embodiment of the applicant's invention relates to a process for producing a stable coagulation control plasma This process includes the sequential steps of collecting the blood from which the plasma is derived directly from an animal source into a solution containing a buffer to maintain physiological pH, a protease inhibitor, and citrate; removing red blood cells from said blood; and adding a suitable stabilizing carbohydrate.

Still another preferred embodiment of this invention relates to a process for producing a stable coagulation control which includes the steps of providing blood plasma; and, adding to said blood plasma at let one purified, stabilized coagulation factor.

DESCRIPTION OF PREFERRED EMBODIMENTS OF THE INVENTIONS

One preferred embodiment of the applicant's invention relates to a stable coagulation control plasma which comprises blood plasma, and effective amounts of (a) a buffer to maintain a physiological pH, (b) a protease inhibitor, and (c) a suitable stabilizing carbohydrate. It is contemplated that a carbohydrate as used herein would have ratios of H to O of 2 to 1, as is understood in the art.

As to types of plasmas which are suitable for this embodiment, primate and non-primate plasmas can be used. Preferred plasmas to date have been human, bovine, porcine, equine and rabbit plasmas, although other plasmas including, for instance, goat and sheep plasmas, can be used. Additionally, in this embodiment of the invention, these plasmas may be collected in any suitable manner as known in the art.

As to the composition of the blood plasma in the control, various animal plasmas may be used individually or combined, adsorbed or non-adsorbed. In most cases, however, the applicant has to date preferred combining the plasmas of two or more types of animal. Since different animals have differing levels and differing stabilities of their respective coagulation factors, different animal plasmas can be selected and combined to adjust the ratios of coagulation factors in the controls and thus also adjust stability of the control and clotting times of the PT, APTT, and other tests.

For instance, owing to their particular coagulation constituent levels, rabbit plasma is used to shorten PT values, porcine plasma is used to shorten APTT but not PT values, bovine plasma is used to furnish high levels of factor V, and equine plasma is used to prolong the APTT but not the PT value. By using these principles, the applicant has been able to prepare, as deed, control plasmas exhibiting particular range (e.g. normal or abnormal) of PT and APTT values. Clotting time can thus be precisely adjusted according to the types and ratios of plasmas used.

Of the preferred control plasmas which have been prepared to date, four have shown to be more preferred. The first exhibits PT and APTT values in the normal range, and has a total plasma component constituted of porcine, bovine and rabbit plasma in ratios of about 1:6:3, respectively. The second has PT and APTT values in the abnormal range and has a total plasma component constituted of porcine plasma adsorbed with aluminum hydroxide gel, and bovine plasma in a ratio of about 35:1, respectively. The third plasma also exhibits PT and APTT times in the abnormal range, and has a total plasma component constituted of porcine plasma adsorbed with aluminum hydroxide gel.

These first three more preferred plasmas provide the advantage of significantly reduced risk of HIV or hepatitis virus infection by those who prepare and/or use them since the pertinent viruses are not present in the non-primate plasmas. Additional advantages have related to high and stable levels of coagulation factors these plasmas have provided. In this regard, it is understood that similar advantages can be derived so long as the non-primate plasma constitutes at least a substantial part of the total plasma component of the control, and thus such control plasmas are also a preferred aspect of this invention, as are controls whose plasma component consists essentially of non-primate plasmas.

The fourth more preferred control has a plasma component constituted of normal human, bovine, and rabbit plasma in respective ratios of about 2:2:1.

With respect to the buffer, to date, HEPES buffer has been preferred, although many other buffers, for instance TRIS, are known and are suitable. The preferred HEPES buffer has been HEPES hemi sodium, which is preferably present in the control in an amount of at least about 0.08 M, and preferrably above 0.05 in amount.

As to amounts and types of protease inhibitor and carbohydrate, it has been preferred to date that the inhibitor and carbohydrate be preset in the control in amounts of at least about 0.5 U/ml, and 2 weight pent, respectively. The preferred protease inhibitor has been apron, although other such protease inhibitors, for instance soya bean trypsin inhibitors, are known in the art and are suitable. The preferred stabilizing carbohydrate to date has been saccharides, and in particular, sucrose, although others well known in the art can also be used. Additionally, it has been more preferred to date that the sucrose be present in the control in an amount of about 5 weight percent.

As to other components of the control plasma of this preferred embodiment, it has also been preferred that the control plasma include thimerosal in an amount of preferrably at least about 0.02 weight part and/or sodium azide in an amount of preferrably at least about 0.08 weight percent.

To formulate a batch of control plasma, approximately 1 part (by volume) of the applicant's preferred buffering and preservative solution described in Example 1 below are combined with about 9 parts plasma. More preferred to date has been to combine approximately 1 part of the applicant's preferred buffering preservative solution with about 9 parts of mixed or unmixed non-primate animal plasma.

Further details of the preparation of the control plasmas of this preferred embodiment, as well as details of their stability, can be found in Examples 1–6 and Tables 1–3 below. Collectively, the control plasmas of this embodiment have generally proven stable, meaning that APTT and PT analyses do not change more than about 10% for at least about 3 days at room temperature, or it least about 8 hours at 37° C.

Additionally, as is particularly detailed in Example 6 below, the coagulation controls of this preferred embodiment have demonstrated increased sensitivity to variations in reagents used in clotting time testing. Example 6 details experiments wherein a coagulation control sample prepared in accordance with this embodiment was tested against a commercially available plasma, CITROL I, and fresh normal human plasma as regards sensitivity to dilutions of thromboplastin reagent in the PT test. As the reported results demonstrate, the control prepared in accordance with the applicant's invention herein demonstrated superior sensitivity to the varying dilutions of thromboplastins.

As stated, another preferred embodiment of the present invention involves a coagulation control plasma having high stabilized levels of Factor V and VIII. This control comprises plasma derived from blood which has been collected directly from an animal source into a collecting solution containing a buffer to maintain physiological pH, a protease inhibitor, and citrate, and to which, after removal of red blood cell, has been added at least about 2 weight percent of a suitable stabilizing carbohydrate.

Although others can be used, to date, the preferred buffer into which the blood has been collected has been HEPES hemi-sodium, and the preferred protease inhibitor has been aprotinin. It has also been preferred that the HEPES hemi-sodium and the aprotinin be present in the collecting solution in respective amounts of at least about 0.25 M and 5 U/ml. Citrate can be present in the collecting solution in suitable amount as known in the art. To date, however, it has been preferred that sodium citrate be present in an amount of about 3 weight percent. When these preferred amounts of HEPES hemi-sodium, aprotinin, and citrate are used, about 9 parts (by volume) blood are preferably collected into about 1 part of the collecting solution.

The carbohydrate can be added in solid form or in solution. Again, the preferred carbohydrate has been sucrose, which has been added after removal of red blood cells from the plasma by centrifuging or another suitable method. Additionally, it has been more preferred to add sucrose to a level of about 5 weight percent in the control. If desired, additional physiological pH buffer can also be added (as a solid or in solution) to effect a desired level in the final control. Preferably, the final control has also contained thimerosal (preferably at least about 0.02 weight percent) and sodium azide (preferably at least about 0.08 weight percent). The thimerosal and/or sodium azide can be present initially in the collecting solution or can be added later as a solid or in solution.

The applicant has discovered that preferred plasmas prepared according to this embodiment are very high in Factor V and VIII content. Additionally, the applicant has found that the Factor V and VIII contents thus produced are highly stable at both room temperature (for at least about 3 days) and at about 37° C. (for at least about 8 hours).

Plasmas which are suitable for this embodiment of the invention include, primate and non-primate plasmas, with preferred plasmas being beef, pig, rabbit, horse, and human plasmas. Additional details of the preparation of control plasmas of this embodiment can be found in Examples 7–11 below.

Another preferred embodiment of the present invention concerns a method for producing a stable coagulation control. As stated above, this method includes the sequential steps of (a) collecting the blood containing the plasma to be used in the control dire from an animal source into a solution containing a buffer effective to maintain a physiological pH, a protean inhibitor, and citrate, (b) removing red blood cells from said blood, and (c) adding at least about 2 weight percent of a suitable stabilizing carbohydrate. Further details of this preferred process are analogous to those discussed in the embodiment immediately above, and can further be found in Examples 7–11 below.

Still another preferred embodiment of this invention concerns a method for producing a stable coagulation control plasma, which method involves the steps Of providing blood plasma, and adding to said plasma at least one stable purified coagulation factor in order to increase the level of the added factor in the plasma. As is further detailed in Example 12 below, particular factors are purified from various animal plasmas as known in the art. These purified factors are then added to plasma to increase the level of the added factor in the plasma and to adjust the PT and/or APTT values. Preferred methods also involve adding to equine or human plasma stable purified Factor V or VIII from bovines or porcines. Additionally, purified equine Factor II has proven particularly stable and can be added to other plasmas as a source of stable Factor II. Collectively, the plasmas to which the stable purified factors have been added have demonstrated stability superior to similar plasmas without the added factors.

Reference will now be made to specific Examples and Tables for the purposes of further describing and understanding the features of the applicant's preferred embodiments as well as their advantages and improvements over the art. It should be understood that them Examples are representative only, and that such additional embodiments and improvements of the same are within the contemplation and scope of the applicant's invention as would occur to one of ordinary skill in this art.

The Factor V and VIII activity values reported in the following Examples were calculated in the conventional manner against a standard curve prepared from dilutions of normal human plasma. PT intends the one-stage prothrombin time, and APTT intends the activated partial thromboplastin time. The PT and APTT tests reported were performed in the conventional manner.

EXAMPLE 1

Preparation of Preferred Preservative Solution 100 ml of the applicant's preferred preservative solution prepared by mixing 500 U aprontinin, about 12.5 g HEPES hemi sodium, 0.1 g thimerosal, 0.5 g $NaN_3$, and 25 g sucrose, and then adding distilled water to 100 ml. This preparation resulted in 100 ml of preservative solution which consisted of:

(a) 0.5 M HEPES hems sodium;

(b) 0.1% thimerosal;

(c) 25% sucrose;

(d) 0.5% sodium azide; and (e) 500 U aprotinin.

EXAMPLE 2

Non-Primate Based Normal Range Control (Level 1)

A pilot lot (hereafter designated P1) of non-primate based control was prepared which demonstrated PT and APTT values in the normal range. Particularly, 54 ml beef plasma, 9 ml pig plasma, and 27 ml rabbit plasma were blended with 10 ml of the preferred preservative solution of Example 1. The initial PT and APTT values were 11.0 and 24.1 seconds, respectively. The lot was divided out into 1.0 ml portions which were placed into individual vials and lyophilized in a conventional manner. A vial of the P1 control plasma was reconstituted the next day with distilled water, whereafter it demonstrated a PT value of 11.0 seconds and an APTT value of 24.1 seconds. Similarly reconstituted P1 vials were allowed to stand at room temperature (about 25° C.) for up to five days, one being tested each day for PT and APTT values. The results are given in TABLE 1 below, and demonstrate excellent stability.

TABLE 1

| Day | 2 | 3 | 4 | 5 |
|---|---|---|---|---|
| PT | 11.2 | 10.8 | 11.7 | 11.2 |
| APTT | 25.7 | 26.2 | 27.1 | 28.3 |

Equally surprising stabilities for Factors V and VIII were shown in the P1 samples. Immediately after reconstitution, P1 samples exhibited Factor V and VIII values of approximately 1000% and 110%, respectively, of the amounts found in normal human plasma pools. After reconstituted samples were allowed to stand for five days at room temperature, they demonstrated a Factor V value of approximately 1100% and a Factor VIII value of approximately 90%.

EXAMPLE 3

Non-Primate Based Abnormal Range Control (Level 2)

A second pilot lot (P2) of control plasma was prepared by combining 175 ml adsorbed pig plasma, 5 ml beef plasma, and 20 ml of the applicant's preferred preservative solution prepared as in Example 1 above. This lot was prepared so as to have abnormal clotting times, with initial PT and APTT values being 21.1 and 40.8, respectively. The P2 lot was divided and lyophilized in the same manner as the P1 lot described in Example 2 above. After reconstitution with distilled water, a vial of the P2 lot produced a PT value of 20.1 and a APTT value of 41.4 seconds.

Analogous to the reconstituted stability tests of Example 2, several reconstituted P2 vials were allowed to stand at room temperature for up to five days with one being tested each day for PT and APTT values. TABLE 2 below sets forth the results which again demonstrate superior stability.

TABLE 2

| Day | 2 | 3 | 4 | 5 |
|---|---|---|---|---|
| PT | 20.6 | 22.0 | 21.6 | 22.7 |
| APTT | 43.8 | 46.1 | 44.1 | 44.4 |

EXAMPLE 4

Non-Primate Based Abnormal Range Control (Level 3)

A third pilot lot (P3) of control plasma was prepared by combining 90 ml adsorbed (with aluminum hydroxide gel) pig plasma with 10 ml of the applicant's preferred preservative solution prepared in accordance with Example 1 above. Initial PT and APTT values of 41.3 and 69.9 were observed for this P3 material. The P3 material was then divided and lyophilized as were the P1 and P2 lot materials of Examples 2 and 3 above. After reconstitution and storage at room temperature for about one day, a vial of P3 material was analyze The PT and APTT values for this reconstituted P3 plasma were 38.1 and 64.1, respectively, showing good stability.

EXAMPLE 5

Human/Non-Primate Normal Range Control 36 ml normal human plasma and 36 ml bovine plasma were combined with 18 ml rabbit plasma and 10 ml of the preservative solution of Example 1 to form a fourth pilot lot (P4) of control material Initial PT and APTT values were in the normal range at 11.4 and 25.7, respectively. This P4 plasma also demonstrated good stability. A reconstituted sample allowed to stand at room temperature for 7 days registered a PT value of 11.5 and an APTT value of 29.7.

EXAMPLE 6

Sensitivity to Reagent Variations

In this Example, the sensitivity of the applicant's preferred control plasmas to variations in clotting time reagents was compared to that of fresh, normal plasma, and to that of CITROL I, a commercially available control plasma marketed by American Dade. The PT test was used in this determination. To perform the study, reagents consisting of 100, 80, 60, 40, 20, and 10% thrombostatin were prepared by diluting the thromboplastin using 0.025 M HEPES buffer, Ph 7.35 containing 0.154 M sodium chloride. These reagent dilutions were then used to evaluate the PT values for the three test plasmas. The results are given in TABLE 3 below. As can be seen, the applicant's P1 control plasma material demonstrated significantly greater variation in PT values resulting from a greater sensitivity to the thromboplastin dilutions. Thus this increases in sensitivity allows detection of defective reagents more readily than even fresh plasma.

TABLE 3

| % Thromboplastin | PT/Fresh Normal Plasma | PT/ CITROL I | PT/ P1 Plasma |
|---|---|---|---|
| 100 | 11.5 | 11.4 | 11.3 |
| 80 | 11.6 | 11.8 | 12.1 |
| 60 | 12.4 | 12.7 | 13.3 |
| 40 | 13.5 | 13.7 | 14.9 |
| 20 | 15.9 | 16.4 | 18.3 |
| 10 | 18.8 | 19.5 | 22.6 |

EXAMPLE 7

Preferred Collecting Solution 100 ml of the applicant's preferred collecting solution were prepared by mixing 500 U aprotinin, about 6.25 g HEPES hemi sodium and 2.94 g sodium citrate, and adding distilled water to 100 ml. This preparation resulted in 100 ml of collecting solution which contained:

(a) 0.25 M HEPES hemi sodium (b) 2.94 gm sodium citrate (c) 500 U aprotinin

Preferably, about 9 parts by volume of blood has been collected into about 1 part by volume of this preferred collecting solution.

EXAMPLES 8–11

Direct Collection into Collecting Solution

In order to obtain a control plasma which has high and stable levels of coagulation Factors, particularly Factors V and VIII, Examples 2–6 are repeated except the plasma used is derived from blood which has been collected directly from the animal source into the applicant's preferred collecting solution of Example 7, and, after removal of red blood cells, sucrose, additional HEPES hemi sodium, as well as thiomersal and sodium azide are added in amounts to achieve the same respective levels as in Examples 2–6. The initial Factor V and VIII activity values are tested and are found to be particularly high as compared to plasmas which are collected into simple conventional citrated anticoagulant solutions. Additionally, the Factor V and VIII values are stabilized by the buffering and preservative solution, as is borne out by high Factor V and VII values obtained after lyophilization and reconstitution, and after reconstituted control plasma samples are allowed to stand at 37° C. for eight hours, and at room temperature for about 3 days. PT and APTT values are similarly stable upon testing after reconstituted control plasmas are subjected to these temperature/time conditions.

EXAMPLE 12

Adding Stable Purified Factors

Pooled normal human plasma was assayed and demonstrated respective APTT and PT values of 34 secs and 13 secs. In various experiments, purified factors X and VIII from pig, cow, horse, sheep or rabbit were added to about 1 ml samples of the normal human plasma and in each instance corrected APTT to 26 secs. Similarly, Factor H from pig, cow, horse, sheep, or rabbit was added to about 1 ml samples of the normal human plasma and corrected PT to 11 secs. Additionally, in each instance, the lyophilized product showed better stability than the lyophilized normal human plasma.

I claim:

1. A method for preparing a coagulation control sample which is stable in the absence of buffer and which has a clotting time within the range of normal human clotting times for reproducibly monitoring coagulation capability in a human patient comprising (a) collecting blood from a mammalian animal, (b) removing red blood cells from said blood to produce mammalian plasma, and (c) adding to the plasma an amount of at least one non-primate mammalian coagulation factor.

2. The method according to claim 1 wherein in step (c) non-primate mammalian plasma is added.

3. The method according to claim 1 wherein said non-primate coagulation factor is selected from the group consisting of equine Factor II, bovine Factor V, swine Factor VIII and combinations thereof.

4. A method for preparing a coagulation control sample which is stable in the absence of buffer and which has a clotting time within the range of abnormal human clotting times for reproducibly monitoring coagulation capability in a human patient comprising (a) collecting blood from a mammalian animal, (b) removing red blood cells from said blood to produce mammalian plasma and (c) adding to the mammalian plasma an amount of at least one non-primate mammalian plasma that has been adsorbed with a coagulation factors II, VII, IX and X adsorbent prior to addition of said plasma to the mammalian plasma.

5. The method according to claim 4 wherein in step (c) non-primate mammalian plasma is added.

6. The method according to claim 4 wherein said non-primate coagulation factor is selected from the group consisting of equine Factor II, bovine Factor V, swine Factor VIII and combinations thereof.

* * * * *

UNITED STATES PATENT AND TRADEMARK OFFICE
CERTIFICATE OF CORRECTION

PATENT NO. : 5,906,942

DATED : 25 May 1999

INVENTOR(S) : Roy E. Speck

It is certified that error appears in the above-identified patent and that said Letters Patent is hereby corrected as shown below:

| Column | Line | |
|--------|------|---|
| 1 | 49 | Change "sp" to --specimens--. |
| 2 | 16 | Change "sum" to --serum--. |
| 4 | 30 | Change "preset" to --present--. |
| 4 | 31 | Change "*pent*" to --percent--. |
| 4 | 32 | Change " apron" to --aprotinin--. |
| 5 | 12 | Change "cell" to --cells--. |
| 5 | 58 | Change "dire" to --directly--. |
| 6 | 1 | Change "Of" to --of--. |
| 6 | 21 | Change "them" to --these--. |
| 7 | 55 | Change "analyze" to --analyzed.--. |

UNITED STATES PATENT AND TRADEMARK OFFICE
CERTIFICATE OF CORRECTION

PATENT NO. : 5,906,942

DATED : 25 May 1999

INVENTOR(S) : Roy E. Speck

Page 2 of 2

It is certified that error appears in the above-identified patent and that said Letters Patent is hereby corrected as shown below:

| Column | Line | |
|--------|------|---|
| 7 | 65 | After "material" insert --.-- |
| 8 | 13 | Change "thrombostatin" to --thromboplastin--. |
| 9 | 16 | Change "Factor H" to --purified Factor II--. |

Signed and Sealed this

First Day of August, 2000

Attest:

Q. TODD DICKINSON

Attesting Officer

Director of Patents and Trademarks